United States Patent [19]

Willemse

[11] Patent Number: 5,144,023
[45] Date of Patent: Sep. 1, 1992

[54] PROCESS FOR THE SYNTHESIS OF POLYOL FATTY ACID ESTERS

[75] Inventor: Gerardus W. M. Willemse, Vlaardingen, Netherlands

[73] Assignee: Van den Bergh Foods Co., Division of Conopco, Inc., Lisle, Ill.

[21] Appl. No.: 794,829

[22] Filed: Nov. 18, 1991

Related U.S. Application Data

[63] Continuation of Ser. No. 278,693, Dec. 1, 1988, abandoned.

[30] Foreign Application Priority Data

Dec. 11, 1987 [GB] United Kingdom ............... 8728960
Sep. 15, 1988 [GB] United Kingdom ............. 8821584.3

[51] Int. Cl.$^5$ .......................................... C07H 13/06
[52] U.S. Cl. .................... 536/124; 536/115; 536/119
[58] Field of Search ............... 536/115, 119, 124; 252/183.11

[56] References Cited

U.S. PATENT DOCUMENTS

| | | | |
|---|---|---|---|
| 2,451,686 | 10/1948 | Möller et al. ................. | 252/187.11 |
| 3,644,333 | 2/1972 | Osipow et al. ................ | 536/119 |
| 3,792,041 | 2/1974 | Yamagishi et al. ............. | 536/119 |
| 3,963,699 | 6/1976 | Rizzi et al. ................... | 536/119 |
| 3,996,206 | 12/1976 | Parker et al. ................. | 536/119 |
| 4,166,173 | 8/1979 | Wurzburg et al. .............. | 252/182 |
| 4,517,360 | 5/1985 | Volpenhein ................... | 536/119 |
| 4,518,772 | 5/1985 | Volpenhein ................... | 526/119 |
| 4,611,055 | 9/1986 | Yamamoto et al. ............ | 536/119 |
| 4,713,436 | 12/1987 | Downs et al. ................. | 536/119 |
| 4,778,881 | 10/1988 | Nieuwenhuis et al. ......... | 536/119 |
| 4,790,962 | 12/1988 | Keulemans et al. ........... | 260/410.7 |
| 4,898,935 | 2/1990 | Nakamura .................... | 536/119 |
| 4,973,682 | 11/1990 | Willemie ...................... | 536/119 |
| 5,006,648 | 4/1991 | Van der Plank et al. ....... | 536/119 |
| 5,071,975 | 10/1991 | Van der Plank et al. ....... | 536/119 |
| 5,079,355 | 1/1992 | Grechke et al. .............. | 526/119 |

FOREIGN PATENT DOCUMENTS

| | | | |
|---|---|---|---|
| 320043 | 6/1989 | European Pat. Off. ......... | 536/119 |
| 47-12 | 1/1972 | Japan .......................... | 536/124 |
| 1-290691 | 11/1989 | Japan .......................... | 536/124 |

*Primary Examiner*—Edward A. Miller
*Attorney, Agent, or Firm*—Gerard J. McGowan, Jr.

[57] ABSTRACT

The invention pertains to a process for the synthesis of polyol fatty acid sters involving transesterification under substantially solvent-free conditions in which the preparation of the starting reaction mixture for the esterification reaction comprises the step of spray-drying. The process provids a very convenient method of desolvatizing and homogenizing the reactants which is economically feasible on a technical scale.

19 Claims, No Drawings

PROCESS FOR THE SYNTHESIS OF POLYOL FATTY ACID ESTERS

This is a continuation, application of Ser. No. 07/278,693, filed Dec. 1, 1988, now abandoned.

The present invention relates to a process for the synthesis of polyol fatty acid esters, wherein a substantially solvent-free reaction mixture of a polyol and/or a fatty acid oligoester thereof, a fatty acid lower-alkylester, a transesterification catalyst and, optionally, an emulsifier is prepared and subsequently caused to react under transesterification conditions.

In this specification the term "polyol" is intended to include any aliphatic or aromatic compound which comprises at least four free hydroxyl groups. In particular such polyols include the group of sugar polyols, which comprise the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, lactose, maltose, raffinose, cellobiose, sucrose, erythritol, mannitol, lactitol, sorbitol, xylitol and α-methylglucoside. A generally used sugar polyol is sucrose.

In this specification the term "polyol fatty acid ester" is intended to include both the group of polyol fatty acid oligoesters, in particular the mono-, di- and trifatty acid esters, and the group of polyol fatty acid polyesters, i.e. the tetra- up to the fully substituted fatty acid polyesters.

In this specification the percentage of polyol hydroxyl groups of the polyol fatty acid polyester that on an average have been esterified with fatty acids, is referred to as the degree of conversion, a degree of conversion of 100% corresponding to the fully esterified polyol.

In this specification the term "fatty acid" refers to $C_8$–$C_{24}$ fatty acids which may be saturated or unsaturated, and may have straight or branched alkyl chains.

The polyol fatty acid oligoesters are well-known for their suitability as emulsifying agents in foodstuffs and detergents, and as drying oils in paint and varnish.

The polyol fatty acid polyesters are known to be suitable low-calorie fat-replacers in edible products. Substantially indigestible for human beings they have physical and organoleptic properties very similar to triglyceride oils and fats conventionally used in edible products. Polyol fatty acid polyesters are further reported to have use as pharmaceutical agents in view of their ability to take up fat-soluble substances, such as in particular cholesterol, in the gastro-intestinal tract, and subsequently remove these substances from the human body.

Processes for the synthesis of polyol fatty acid esters using transesterification techniques are well known. Examples of such processes are described e.g. in U.S. Pat. Nos. 3,963,699, 4,517,360 and 4,518,772. In the art it has been well recognised that catalytic transesterification to prepare food-grade polyol fatty acid esters is advantageously influenced by using as starting reactant mixture a solvent-free homogeneous melt of the reactants. Up to now the methods to prepare such solvent-free homogeneous reactant mixtures have not been fully satisfactory, particularly in terms of economic applicability on a technical scale.

In this specification the term "homogeneous" means intimately mixed, and is not restricted to homogeneous in a narrow microscopic sense.

It is now an object of the present invention to provide an improved process for the synthesis of polyol fatty acid esters, particularly with respect to the preparation of a suitable substantially solvent-free starting mixture of reactants which allows, on a technical scale, simplicity of processing and a continuous or semi-continuous operation without adverse effects on conversion rates of polyol to polyol ester or polyester.

Accordingly, the invention provides a process for the synthesis of polyol fatty acid esters, wherein a substantially solvent-free reaction mixture of a polyol and/or a fatty acid oligoester thereof, a fatty acid lower-alkylester, a transesterification catalyst and, optionally, an emulsifier is prepared and subsequently caused to react under transesterification conditions, the preparation of the substantially solvent-free mixture comprising the steps of (1) forming a mixture of the polyol and/or fatty acid oligoester thereof, the fatty acid lower-alkylester, the transesterification catalyst, and, optionally, the emulsifier or precursor thereof, and one or more solvents, and (2) homogenizing and desolvatizing the mixture formed in step (1) by way of spray-drying.

The preparation of a substantially solvent-free homogeneous mixture of reactants in accordance with the invention may be advantageously applied to all transesterification processes for the preparation of polyol fatty acid polyesters, where a substantially solvent-free homogeneous reactant mixture is necessary or desired.

The reactants which are mixed in the first step of the preparation of the substantially solvent-free reactant mixture comprise a polyol and/or a fatty acid oligoester thereof, a fatty acid lower-alkylester, a transesterification catalyst and, optionally, an emulsifier, such as a fatty acid soap. Also, solvents, such as water and/or lower-alkyl alcohols, may optionally be introduced separate from or together with one or more of these reactants.

The polyol can be any of those as defined hereinbefore, or a mixture thereof. Preferred polyol starting materials are the sugar polyols, and in particular sucrose. The polyol starting material does not necessarily consist solely of non-esterified polyols. It may in addition, or even solely, comprise polyol oligoesters of fatty acids, such as mono-, di- and/or triesters, which are intermediates in the conversion of polyols to the polyol fatty acid polyesters.

Suitable fatty acid lower-alkylesters are fatty acid esters of the group of lower alcohols including mono-, di- and triols. In particular, the ester is derived from the $C_1$–$C_5$ mono-alcohols, preferably methanol. The fatty acid residues can be any of those as defined hereinbefore, the selection of which is dependent of the specific polyol fatty acid esters desired.

The amount of fatty acid lower-alkylester is dependent on the desired degree of conversion. In the synthesis of polyol polyesters having high degrees of conversion in general excess amounts of fatty acid lower-alkylester are used. More particularly, when fully converted sucrose polyesters are aimed at, good results are obtained when a molar ratio of fatty acid lower-alkylester: sucrose is used within the range of from 10:1 to 20:1, in particular, of from 10:1 to 15:1, or even 10:1 to 14:1.

Suitable transesterification catalysts include the group consisting of alkali metals, alkaline earth metals, and alloys thereof, as well as the alkoxides, bicarbonates, carbonates, hydrides, and hydroxides of such metals. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

The catalyst is used in an amount corresponding to a molar ratio of catalyst: polyol of at least 0.01:1, and preferably of 0.05:1 to 1:1.

In general it is attractive to use an emulsifier to improve contact between the polyol, the catalyst and the fatty acid lower-alkylester particularly during the initial stages of the esterification reaction. Many types of alkali-resistant emulsifiers can suitably be used, such as edible emulsifiers including phosphatides, such as lecithin, mono- and diglycerides and sugar oligoesters of fatty acids, in particular the mono- and diesters, and detergents, such as soaps and alkali metal alkyl sulphates.

Preferred emulsifiers are alkali metal soaps derived from any of the fatty acids as defined hereinbefore. It has been found that conversion rates of polyol to polyol fatty acid ester are improved when fatty acid soap emulsifiers are used comprising at least 15%, but preferably even at least 75% of short chain fatty acid soap. Such short chain fatty acid soap is characterized by a fatty acid chain length of less than 15 carbon atoms, and in particular within the range of 6 to 12 carbon atoms, such as coconut soap.

Particularly, when the emulsifier is selected from the group of alkali metal soaps, it may be convenient to introduce the emulsifier into the mix of step (1) of the process of the invention in the form of a precursor thereof, such as the corresponding free fatty acids. In such a case the composition of the reactant mixture should be such that the precursor is converted to the corresponding emulsifier after addition to and mixing with the reactant mixture.

When free fatty acids are used as emulsifier precursors, an alkaline material should be present in the reaction mixture suitable to convert the fatty acid precursor into the corresponding soap emulsifier. Suitably, the transesterification catalyst can be used to effectuate such a conversion. Accordingly, the amount of catalyst introduced in the mixture before the spray-drying in accordance with the invention should be sufficient to ensure both proper catalytic action during the esterification, as discussed hereinbefore, and full neutralization of such a soap precursor to the corresponding soap.

Suitable amounts of emulsifier lie within the range of from 0.1 to 15% by weight, preferably of from 0.1 to 12%, and most preferably of from 0.2 to 6% by weight of the total reactant mixture.

Optionally, one or more solvents may be introduced separate from or together with the various reactants to improve addition and mixing thereof. Suitable solvents include water and/or lower alcohols, such as $C_1$-$C_5$ alcohols, in particular methanol.

An essential feature of the present invention is spray-drying the reactants mixed together in the first step of the preparation to achieve a homogenized and substantially solvent-free reaction mixture particularly suitable as starting mixture for the subsequent esterification reaction.

By substantially solvent-free reaction mixture is meant a mixture comprising less than 0.5% of solvent, solvent levels at the start of the transesterification reaction of less than 0.1 or even 0.05% being preferred.

Spray-drying may be carried out in conventional manner by passing the mixture through a spraying nozzle into a drying chamber. Homogenization of the mixture occurs due to the dissipation of energy on passing through the nozzle. The amount of energy dissipated, and accordingly the degree of homogeneity in the sprayed mixture, is a function of the design of the spraying nozzle and the pressure applied to the mixture before the nozzle. In the art numerous designs and corresponding spraying conditions are known and available. Suitable types of spraying nozzles include hollow- and full-cone nozzles, fan-spray nozzles, pneumatic nozzles with internal- or external-mixing, and rotary (-disc) atomizers.

Resulting in the substantially solvent-free mixture, evaporation and removal of the solvent, which may be present in the combined reactants either due to specific introduction to facilitate addition of one or more of the components or simply stemming from the use of non fully dry components, occurs in the drying chamber, the resulting vapour continuously being removed from the drying chamber by suitable reduced pressure or gas flow conditions. Adequate solvent evaporation may be established by a variety of per se conventional techniques, including the application of reduced pressure and/or elevated temperature conditions, or the use of, optionally heated, co-current, counter-current or mixed-current inert gas flows. Suitable chamber dimensions strongly depend on the spraying nozzle and temperature, pressure and flow conditions applied.

Suitably the reaction mixture is fed to the spray-drying nozzle being heated to a temperature adequate to provide the latent heat necessary for the evaporation of the solvent. Dependent on the resistance of the reaction mixture to side-reactions such temperatures lie within the range of from 110° to 180° C., the temperature range of from 120° to 150° C., particularly to 140° C. being preferred.

In a batch-wise operation the drying chamber is also suitably used as reaction vessel for the transesterification reaction. In a continuous or semi-continuous operation the drying chamber and reaction vessel preferably are separate.

It may be of further advantage to pre-homogenize the mixture before it is passed through the spraying nozzle by an alternative agitation step for example employing a dynamic or static mixer, or flow restriction in the feed line to the spraying nozzle.

In a preferred embodiment of the invention the reactant mixture is prepared by way of the following process.

In an initial step the polyol or the fatty acid oligoester thereof is mixed with the catalyst in a liquid system so as to form the corresponding polyol anion. The formation of the actual polyol anion may be immediate or only be realized under substantially solvent-free conditions. Preferably, the contact between the polyol or the oligoester thereof and the catalyst are mixed in the presence of a solvent, which is subsequently removed in the spray-drying step in accordance with the present invention. Most preferably, the polyol or the oligoester thereof and the catalyst are first partially or fully dissolved in a solvent and subsequently mixed. Suitable such solvents include water, lower alcohols and mixtures thereof. In particular water is a suitable solvent if potassium or sodium hydroxide is used as the transesterification catalyst.

In a subsequent step the fatty acid lower-alkylester, optionally in combination with the emulsifier, is added to the liquid system. After addition of the fatty acid lower-alkylester the reaction mixture is spray-dried in accordance with the present invention.

As stated hereinbefore alkali metal soaps or suitable precursors thereof such as the corresponding free fatty acids are preferred emulsifiers particularly to assist in the start-up and initial stages of the esterification reaction. Although very suitable in terms of the esterification reaction a drawback that may be attached to the use of soaps is the fact that the spray-drying thereof necessitates relatively frequent cleaning of the spray-drying equipment. In particular on a technical scale this is undesirable.

It has been found that the emulsifier component, and in particular soap emulsifiers or precursors thereof can suitably be added to the reaction mixture after the spray-drying step in accordance with the invention. Using this route the relatively frequent cleaning of the spray-drying equipment can be avoided.

Preferably, the emulsifier or the precursor thereof is added to the reaction mixture while applying some agitation to ensure thorough mixing. Such agitation is suitably achieved by stirring, by employing a dynamic or static mixer, or by simultaneous mixing and pumping.

The degree to which desolvatization is achieved in the spray-drying step, is the resultant of economic and process-technical factors, such as in particular the amount of solvent to be removed and the corresponding energy input or temperature required in the drying chamber.

Accordingly, instead of using spray-drying conditions resulting in full removal of solvent, it may be of advantage to have the spray-drying step followed by a further 'post-drying' treatment which drives the removal of residual solvent to substantial completion. Any such conditions resulting in evaporation of any residual solvent still present after spray-drying or introduced in the post spray-drying addition of the emulsifier component, may be suitable and include temperature and reduced pressure conditions, stripping with suitable stripping agents, such as preferably methanol, or inert gases, such as nitrogen, or submitting the reaction mixture to a further spray-drying step.

Preferably, the reaction mixture is submitted to conditions of elevated temperature and reduced pressure suitable for drying. Drying temperatures lie below about 110° C. and preferably within the range of 60° to 100° C. Suitably, these post-drying conditions are maintained for periods of up to several hours, periods of 0.5 to 3 hours being preferred.

Suitably the solvent level of the reaction mixture is reduced to below 0.5% in the spray-drying step and further reduced to below 0.1% in the subsequent post-drying step. Preferably, the solvent level is reduced to below 0.1% in the spray-drying step and to below 0.05% in the post-drying step.

The process of the invention thus allows preparation of a suitable starting reaction mixture for subsequent transesterification reactions which can be carried out both batchwise and continuously and is economically feasible on a technical scale.

The substantially solvent-free reaction mixture prepared according to the present invention is subsequently further reacted under suitable conditions to cause transesterification to the desired polyol fatty acid esters.

In general, the transesterification reaction is carried out at elevated temperature, in particular, in the range of from 100°–180° C., a temperature in the range of 110°–160° C. being preferred, temperatures in the range of from 120° to 150° C. being preferred most. In the case the reaction mixture is submitted to a the transesterification reaction preceding post-drying step, the transfer from the post-drying to the reaction temperature regime may be stepwise, but conveniently can be carried out by gradually raise of the temperature.

The reaction is preferably carried out under such conditions that the alcohols formed in the transesterification, are removed during the reaction. To this purpose the reaction is advantageously carried out at reduced pressure. Very suitably, during the esterification a pressure profile is used to drive the esterification to the desired degree of conversion as described in our co-pending GB Patent Application No. 8730266 incorporated herein by reference.

Although the process of the present invention is suitable for the synthesis of polyol fatty acid esters of the general group as defined hereinbefore, it is particularly suitable for the synthesis of polyol fatty acid polyesters having a degree of conversion of over 80%, or even 90%. In particular, such polyesters derived from the sugar polyols selected from the group of disaccharides or the alcohol derivatives thereof, such as sucrose, and esterified to over 95% degree of conversion, are suitably synthesized by the method in accordance with the present invention.

Preferred embodiments of the invention will now be illustrated with reference to the following examples, all percentages being by weight unless indicated otherwise.

EXAMPLE 1

In a supply vessel fatty acid methylester (derived from soya bean oil fatty acids) was mixed with coconut fatty acids in a weight ratio of 100:4.5. This mixture was pumped through a heat-exchanger at a rate of 60 kg/hour and heated to about 135° C. Subsequently, an 50% w/w aqueous solution of KOH was introduced in-line into the mixture by pump at a rate of 1700 grams/hour (excess KOH to saponify all of the coconut fatty acids). The resulting mixture was passed through a spraying nozzle into a drying chamber under reduced pressure conditions of 5–10 mbar. The spray-dried mixture (methylester/soap dispersion) consisted of about 94% by weight of the fatty acid methylester, about 6 % by weight of potassium soaps, and less than 0.01% by weight of water. Subsequently, this methylester/soap dispersion was mixed with about an equal amount by weight of the methylester.

The resulting methylester/soap dispersion was pumped through a second heat-exchanger at a rate of 60 kg/hour and re-heated to 135° C. Subsequently, a previously prepared aqueous sucrose/KOH solution was introduced in-line into the ester/soap dispersion by pump at a rate of 2125 grams/hour. The sucrose/KOH solution was prepared by combining about 54 parts by weight of sucrose, about 29 parts by weight of water and about 17 parts by weight of a 50% w/w aqueous solution of KOH. The resulting reactant mixture was passed through a second spraying nozzle into a drying chamber under reduced pressure conditions of 5–10 mbar.

After spray-drying the reaction mixture consisted of about 95% by weight of the fatty acid methylester, 3% by weight of the potassium soap, 2% by weight of K-sucrate, and less than 0.1% by weight of water.

To this mixture a supplementary amount of about 5% by weight of sucrose was added, after which the reactant mixture was suitably further reacted under conventional transesterification conditions.

EXAMPLE 2

From a supply vessel fatty acid methylester (derived from soya bean oil fatty acids) was pumped through a heat-exchanger (temperature 145° C.) and a dynamic mixer at a rate of 60 kg/hour. An aqueous solution prepared from mixing a 70% sucrose solution and a 50% KOH solution (mixing ratio of 85:15 by weight) was introduced separately into the dynamic mixer at a rate of 8 kg/hour. From the dynamic mixer the combined and mixed streams of methylesters and sucrose/KOH solution were fed to a spray-drying device and spray-dried to 0.08% water at 5 mbar. Subsequently, using vigorous stirring distilled coconut fatty acids were added to the spray-dried mixture at a temperature of 60° C. and atmospheric pressure. For a period of two hours the resulting mixture was then post-dried under vacuum at a temperature going up to 90° C. The then substantially solvent-free mixture (composition: 90% methylesters, 3% soap, 7% sucrose including 2% potassium sucrate) was subsequently esterified at a temperature of 130°-140° C. and a pressure of 120 mbar gradually going down to 1 mbar during the course of the reaction. During the final two hours the esterification reaction was driven to completion using hexane to strip the methanol. After completion of the esterification reaction, but before refining, the composition was as follows:

| | |
|---|---|
| methylester | 44.0% |
| soap | 4.5% |
| sucrose fatty acid polyester | 46.0% |
| (degree of conversion: over 98%) | |
| minor impurities(*) | 5.5% |

(*)mainly mono-, di- and triglycerides stemming from the initial methylester

I claim:

1. A process for the synthesis of polyol fatty acid polyesters which comprises the steps of
   (1) forming a mixture of one or more polyol compounds selected from the group of sugar polyols having at least 4 free hydroxyl groups, and fatty acid oligoesters thereof, a $C_8$ to $C_{24}$ fatty acid lower-alkylester, a transesterification catalyst, and one or more solvents,
   (2) homogenizing and removing the one or more solvents from the mixture by spray drying and
   (3) reacting the solvent-free mixture under transesterification conditions.

2. The process according to claim 1 comprising the further step of agitating the mixture formed in step (1) before the spray-drying step.

3. The process according to claim 1 wherein the catalyst is selected from the group consisting of hydroxides, carbonates and bicarbonates of potassium and sodium.

4. The process according to claim 1 wherein the fatty acid lower-alkylester is a fatty acid methylester.

5. The process according to claim 1 which further comprises the step of introducing an emulsifier or precursor thereof into the mixture prior to step (3).

6. A process according to claim 5 wherein the emulsifier is an alkali metal soap.

7. The process according to claim 6 wherein the alkali metal soap is selected from the group of short chain soaps having a chain length within the range of from 6 to 12 carbon atoms.

8. The process according to claim 5 wherein the precursor is selected from the group of free fatty acids.

9. The claim according to claim 8 wherein the catalyst is introduced in an amount sufficient for both catalytic action and neutralization of the free fatty acids to the corresponding soap.

10. The process according to claim 1 wherein step (1) comprises the steps of:
    (a) first mixing the one or more polyol compounds and the catalyst in a liquid system; and
    (b) subsequently adding to the liquid system the fatty acid lower-alkylester.

11. The process according to claim 10 wherein the liquid system of step (a) comprises a solvent.

12. The process according to claim 11 wherein the catalyst is an alkali metal hydroxide and the solvent is water.

13. The process according to claim 1 wherein the solvent-free mixture is reacted until polyol fatty acid polyesters having a degree of conversion of over 90% are obtained.

14. The process according to claim 1 wherein the molar ratio between the fatty acid lower-alkylester and the one or more polyol compounds is within the range of from 10:1 to 15:1.

15. The process according to claim 14 wherein the polyol is sucrose.

16. The process according to claim 5 comprising the step of introducing the emulsifier or precursor thereof into the mixture after the spray-drying step.

17. The process according to claim 1 which comprises a further drying treatment after the spray-drying step.

18. The process according to claim 1, wherein the mixture of step (1) also includes an emulsifier.

19. The process according to claim 10 wherein the fatty acid lower alkyl ester which is added is in combination with an emulsifier.

* * * * *